(12) United States Patent
Wang et al.

(10) Patent No.: US 8,653,298 B2
(45) Date of Patent: Feb. 18, 2014

(54) BIPHENYL ACETATE, PREPARATION AND USES THEREOF

(75) Inventors: Wei Wang, Guangdong (CN); Wenzhan Chen, Guangdong (CN)

(73) Assignee: Shijiazhuang Yiling Pharmaceutical Co., Ltd., Shijiazhuang, Hebei Province (CN)

( * ) Notice: Subject to any disclaimer, the term of this patent is extended or adjusted under 35 U.S.C. 154(b) by 809 days.

(21) Appl. No.: 12/309,326

(22) PCT Filed: Sep. 27, 2007

(86) PCT No.: PCT/CN2007/002830
§ 371 (c)(1),
(2), (4) Date: Jan. 12, 2009

(87) PCT Pub. No.: WO2008/049317
PCT Pub. Date: May 2, 2008

(65) Prior Publication Data
US 2010/0016632 A1  Jan. 21, 2010

(30) Foreign Application Priority Data
Oct. 23, 2006  (CN) .......................... 2006 1 0122917

(51) Int. Cl.
*C07C 229/00*  (2006.01)
(52) U.S. Cl.
USPC ........................................................ 562/452

(58) Field of Classification Search
None
See application file for complete search history.

(56) References Cited

U.S. PATENT DOCUMENTS

| 3,784,704 A * | 1/1974 | Cohen et al. .................. 514/570 |
| 2004/0249158 A1 * | 12/2004 | Wells et al. .................. 546/122 |
| 2005/0065196 A1 * | 3/2005 | Inaba et al. .................. 514/365 |
| 2005/0119314 A1 * | 6/2005 | Inaba et al. .................. 514/340 |
| 2005/0153419 A1 * | 7/2005 | Liu et al. .................... 435/235.1 |

FOREIGN PATENT DOCUMENTS

| EP | 0264552 | * | 4/1988 |
| EP | 264552 | * | 4/1988 |

OTHER PUBLICATIONS http://en.wikipedia.org/wiki/Dissociation_(chemistry), pp. 1-3, downloaded Apr. 4, 2012.*

* cited by examiner

*Primary Examiner* — Johann R Richter
*Assistant Examiner* — Jennifer C Sawyer
(74) *Attorney, Agent, or Firm* — Novoclaims Patent Services, LLC; Mei Lin Wong

(57) ABSTRACT

The biphenyl acetate is biphenyl acetic ammonia butantriol salt, which is obtained by reacting biphenyl acetic acid with ammonia butantriol in organic solvent. The salt is adapted to be used for producing analgesic, anti-inflammatory and antithermic medicines.

13 Claims, 3 Drawing Sheets

BIPHENYL ACETATE, PREPARATION AND USES THEREOF

BACKGROUND OF THE PRESENT INVENTION

1. Field of Invention

The present invention relates to preparation and use of biphenyl acetate, and more particularly to a preparation and use of biphenyl acetic ammonia butantriol salt.

2. Description of Related Arts

In 1993, biphenyl acetic acid is commonly used as a medicine for reducing inflammation and relieving pain in Japan and Italy, and further use for metaboly arthritis, omarthritis, tenosynovitis, muscle pain, and cartilage tissue injury. In addition, it also use for reducing traumatic swelling and pain. Because of the insolubility of water, biphenyl acetate only can use for traumatic medicine. This property restricts the application of this medicine. In Japan, biphenyl ethyl acetate has been used for injecting emulsion (insolubility of water) of reducing clinical pain. Recently, the production company recalls this variety emulsion, because the emulsion may cause a shock in clinic from allergy. The coemulsifier of injecting emulsion acts as one of the allergen is soy phosphatidoo. Therefore, the biphenyl ethyl acetate which acts as emulsion has low stability, producing technique re-staining, and the unsafe deficiency of big molecule's coemulsifier.

SUMMARY OF THE PRESENT INVENTION

A main object of the present invention is to provide a new kind of biphenyl acetate, which is biphenyl acetic ammonia butantriol salt. The biphenyl acetic ammonia butantriol salt has the following chemical structure.

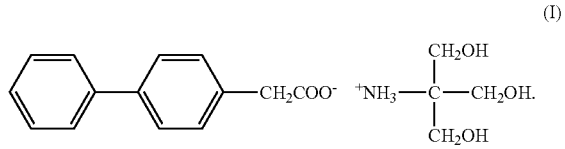

Its molecular structure is $C_{18}H_{23}NO_5$, and its molecular weight is 333.14.

Another object of the present invention is to provide a manufacturing method of biphenyl acetic ammonia butantriol salt. This method is to react biphenyl phenylacetic acid with ammonia butantriol in organic solvent, and then generate biphenyl acetic ammonia butantriol salt. The reaction formula is below:

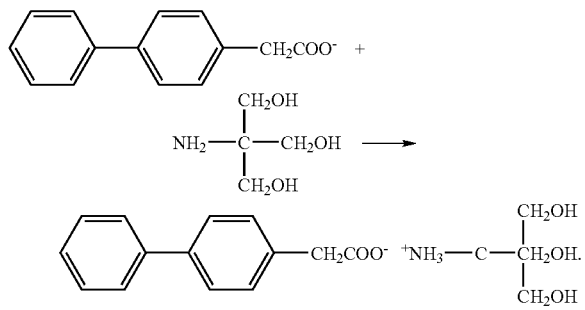

In the method above, it is available to add biphenyl phenylacetic acid with ammonia butantriol at the same time in organic solvent, or add biphenyl phenylacetic acid first. It is also available to add ammonia butantriol first in organic solvent, and then react with biphenyl phenylacetic acid to generate biphenyl acetic ammonia butantriol salt. In order to increase recovery rate, the ratio of biphenyl phenylacetic acid and ammonia butantriol should be 1:1. As for organic solvent, this organic solvent should have the ability to dissolve phenyl acetic acid, such as alcohol and benzene, and especially chose methanol, anhydrous ethanol, acetone, and n-butanol, benzyl and benzene. In the method above, there are not any special requirement for temperature and time. The normal reaction temperature is 0-80° C., but it prefers to set the temperature at 50-70° C. The reaction time is 0.5-2 hours.

The method also includes the procedure of the purification of biphenyl acetic ammonia butantriol salt. There are variety purification methods that we can use today, and here are two classic purification method: the first one is to evaporate solvent, and then generate the white powder after the reaction. Further, the procedure is to dry the white powder in vacuum, and then generate biphenyl acetic ammonia butantriol salt. The other method is to cool down the solvent below 0° C., and then generate crystallization. Consequently, we dry the crystallization in vacuum to produce biphenyl acetic ammonia butantriol salt. The second method is the best way to use, because it can get the better compound's purity and crystal analgesic.

According to the above manufacturing method, the yield of biphenyl acetic ammonia butantriol salt is 85.6-96%, and the purity is 99.2-99.8%. Further, the melting point is 162-163° C.

Another object of the present invention is to provide the pharmaceutics application of biphenyl acetic ammonia butantriol salt. As for the research, this biphenyl acetic ammonia butantriol salt has anti-inflammatory, analgesic, and antipyretic. Accordingly, the subject matter of the present invention is the active compound of biphenyl acetic ammonia butantriol salt.

If the purpose require, we can add one or more kinds of accepting carrier in this medicine, including diluting agent, excipient, extender, adhesive, moistening agent, disintegrating agent, absorbefacient, surfactant, adsorption agent, and lubricant. This medicine also can add scenting agent, sweetening agent and so on.

This medicine can be manufactured as injection (injective liquid, injective cool powder, and injective aseptic needle), tablet, powder, pill, capsule, oral liquid, cream, and so on. These above kinds of medicines all can be manufactured in terms of the normal order in pharmaceutical field. The amount of taking this biphenyl acetic ammonia butantriol salt medicine is 0.8-3.6 mg/ kg/days.

These and other objectives, features, and advantages of the present invention will become apparent from the following detailed description, the accompanying drawings, and the appended claims.

DETAILED DESCRIPTION OF THE PREFERRED EMBODIMENT

Figure 1:
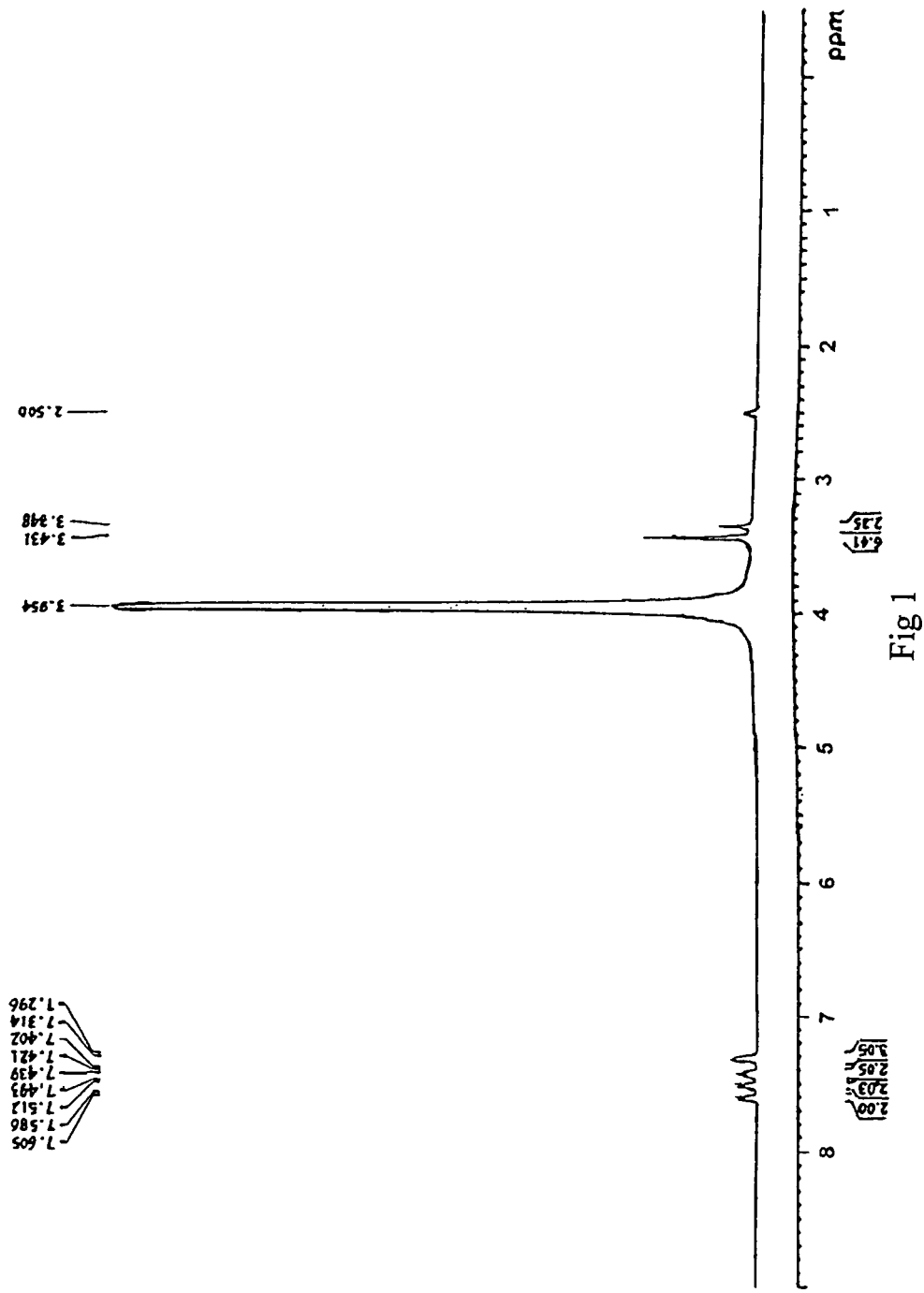
FIG. 1 is the HNMR spectroscopy analysis of biphenyl acetate according to a preferred embodiment of the present invention.

Table 1 illustrates solubility testing; Table 2 illustrates the analgesia affection of mice heating plate method's for injecting the biphenyl acetic ammonia butantriol salt liquid; Table 3 illustrates the affection of expansion in Kunming's mouse for biphenyl acetic ammonia butantriol salt injection in dimethyl benzene; Table 4 illustrates the affection of expansion in Kunming's mouse for biphenyl acetic ammonia butantriol salt injection glacial acetic acid; Table 5 illustrates allergic reaction symptom; Table 6 illustrates allergenicity evaluation standard of cavia porcellus; Table 7 illustrates the active allergic testing of animals' change condition in cavia porcellus for injects the biphenyl acetic ammonia butantriol salt injection; Table 8 illustrates allergic reaction condition of the whole body active allergic testing in injecting the biphenyl acetic ammonia butantriol salt injection; Table 9 illustrates the number of 2% red blood cell's suspending liquid; Table 10 illustrates the result of hemolytic testing (application of visual) of the biphenyl acetic ammonia butantriol salt injection (high amount) (ml); Table 11 illustrates the result of hemolytic testing (application of visual) of the biphenyl acetic ammonia butantriol salt injection (low amount) (m1)); Table 12 illustrates the exciting reaction of rabbits' ear for the biphenyl acetic ammonia butantriol salt injection (Application of visual after 48 hours regent time); Table 13 illustrates the exciting reaction of rabbits' ear for the biphenyl acetic ammonia butantriol salt injection (Application of visual after 48 hours' last reagent time); Table 14 illustrates the exciting reaction of rabbits' muscle (Application of visual) for the biphenyl acetic ammonia butantriol salt injection (high amount); Table 15 illustrates the exciting reaction of rabbits' muscle (Application of visual) for the biphenyl acetic ammonia butantriol salt injection (low amount); Table 16 illustrates the exciting reaction of rabbits' muscle (sickness investigation) for the biphenyl acetic ammonia butantriol salt injection (high amount); Table 17 illustrates the exciting reaction of rabbits' muscle (sickness investigation) for the biphenyl acetic ammonia butantriol salt injection (low amount); and Table 18 illustrates the test of stomach channel.

The following description illustrates a preparation of biphenyl acetic ammonia butantriol salt according to a first preferred embodiment of the present invention.

21.2 g (0.1 ml) of Biphenyl acetate and 210 ml of methanol are added into a dry and clean 250 ml three opening round bottom crucible bottle. Stir and heat the mixture to 60° C. until the mixture is totally dissolved. Add ammonia butantriol into the mixture solution until the solution is in a clarified transparent manner. Stir the solution for one hour and make TLC fully reacting with the solution. (eluent:DMF-acetic ester 2:1). Set the end point when the raw material biphenyl acetate is totally reacted with another reactants. Cool down to −5° C. for 5 hours and get huge amount of white crystal. Remove chloride and put the solution into vacuum dry machine at 80° C. Finally, we can get the biphenyl acetic ammonia butantriol salt in a white crystal manner. The melting point thereof is between 162 and 163° C. The yield is 91.6%. The theoretical value of element analysis is C: 64.9%; H: 6.9%; N: 4.2%; O: 24%. The actual value of element analysis is C: 64.1%; H: 7.3%; N: 3.6%l O: 25%)

FIG. 1 shows the $^1$HNMR spectroscopy analysis of biphenyl acetate.

There are eight hydrogen peaks signal in the $^1$HNMR spectroscopy of the biphenyl acetate in the solvent of DMSO-d6. According to the chemical shift in HNMR spectroscopy, all peaks' chemical shift ($\delta$) below 4 ppm are H signal of saturated carbon, and the total sum of peaks are 14. Therefore, if $\delta$ value is smaller than 6 ppm, there are all H signal of aromatic ring, and the total number of these peaks is 9. At $\delta=3.35$ ppm, the 2H single hydrogen peak cab be determined as an isolated $CH_2$ group. In the structure of biphenyl acetate, the carbon No. 13 which connects with benzene and COO— in CH2 does not accept the coupling of other hydrogen's core. At $\delta=3.43$ ppm, the 3H single peak cab be determined as three equal value isolated $CH_2$ group. In the structure of biphenyl acetate, carbon NOs. 18, 19, 20 all connect with the carbon No. 17. of the $CH_2$, and these three $CH_2$ are equal values. Because of these three $CH_2$ does not accept the coupling and have the equal value, it reveals single peak signal. The wide peak at $\delta=3.43$ ppm can be determined as three OH group and a protonation's $NH_3+$, because these active H probably combine with the water which is in the solvent, it reveals a wider peak. The integral value can not explain the real number of these active H, because there is water in this solvent. There are four splitting signal groups in the low magnetic field, and according to these peaks' area it only can be known that there are 3, 2, 2, 2, H from high to low magnetic field. Further, there are only three left groups which can be clarify their peak shape, so they can be clarified as two duplicate and one triple peaks. In addition, it can be explained that there are H on the benzene due to their chemical shift, so two duplicate peaks near 8.0 Hz which named ad peak No. 7 and No. 8 can indicate as two positions. One position is on a side of benzene which has H, and the other is a side of benzene which does not have H but have other substituted group. The two duplicate peaks can be explained as four H in the structure of biphenyl acetate which are H2/H6, H3/H5, and H8/H12. Furthermore, the triple peaks near by 7.6 Hz can be explained as positions that those benzenes have H on their both side, and there are H9, H10, and H11 in this molecular structure.

Figure 2:
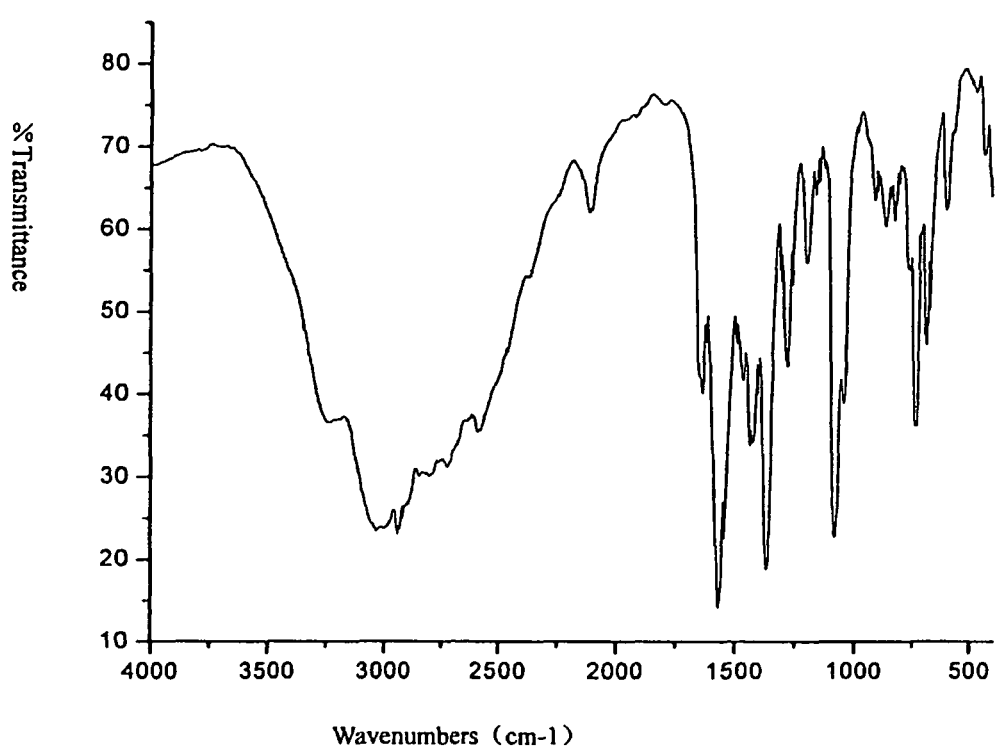
FIG. 2 is the IR spectroscopy analysis of biphenyl acetate according to the above preferred embodiment of the present invention.

IR spectroscopy analysis of biphenyl acetate is shown in FIG. 2.

(1) It can be determined the structure of this molecule has amine salts of carboxylic acids, if there is a wide and strong COO— stretching vibration peak at 1560.13 $cm^{-1}$, and wide, strong, and scattered $NH_3+$ characteristic peak at the region of 2927.41-2113.60 $cm^{-1}$. The COO— and $NH_3+$ form a COO—. $NH_3+$ free monomer molecular structure, and COO— and $NH_3+$ also easily form hydrogen bonds between dimmer to polymer. In addition, the stretching vibration frequency region of $NH_3+$ and OH of $CH_2$—OH reveal at 2927.41-2113.60 $cm^{-1}$, and then form multiple, overlapping, scattered, and strong peaks.

(2) The stretching vibration wide strong peak of OH is at 3214.94 $cm^{-1}$. The other deformed vibrations about OH group ($\delta$ OH) are at 1423.21 $cm^{-1}$ and 1278.57 $cm^{-1}$, and further a flat shaking vibration is at about 690.39 $cm^{-1}$ (rOH). It can be explained that the wide, strong, and stretching vibration peak at 1083.80 $cm^{-1}$, is C—O (vC—O), so it also can declare that OH directly connect with $CH_2$.

(3) The series spectrum peaks at 2987~2896 $cm^{-1}$, which are determined there are saturated carbon hydrogen group in this molecular structure, are both the asymmetric and symmetric stretching vibration group, such as $CH_3$ and $CH_2$. At the same time, the deformed absorbing vibration of $CH_3$ and $CH_2$ reveal at the region of 1467~1367 $cm^{-1}$. Even though, it can be reasoned from NMR spectrum that this compound does not contain methyl, there are some disrupted peaks near by 2965±$cm^{-1}$ and 1375±$cm^{-1}$ from IR, so it can not be clarify that this compound does not include methyl.

(4) At 3100~2980$cm^{-1}$, there are a series of peaks that can be declared this molecular structure has unsaturated hydrocarbon group, such as aromatic ring, benzene ring, and alkene structure. At 1650~1423cm$^{-1}$, there are many unsaturated group that can be determined as C=C and C=N. At 1201~977 cm$^{-1}$, it can be determined that has an internal bending vibration (β) of =CH group in benzene. At 738.6 and 690.39 cm$^{-1}$, it can be determined that has two outer bending strong vibration peaks of monosubstituted benzene ring (γ). At the region of 2000-1666 cm$^{-1}$, a series' peaks in this region are the same as the overlapping and combined of a monosubstituted benzene ring and a p-disubstituted benzene ring.

(5) There is stretching vibration of amine salt's C—N bond which reveals at 1045.2 cm$^{-1}$, and further, there is an outer bending vibration (γ) of NH$_3$+ reveals at 605.5 cm$^{-1}$.

Figure 3:
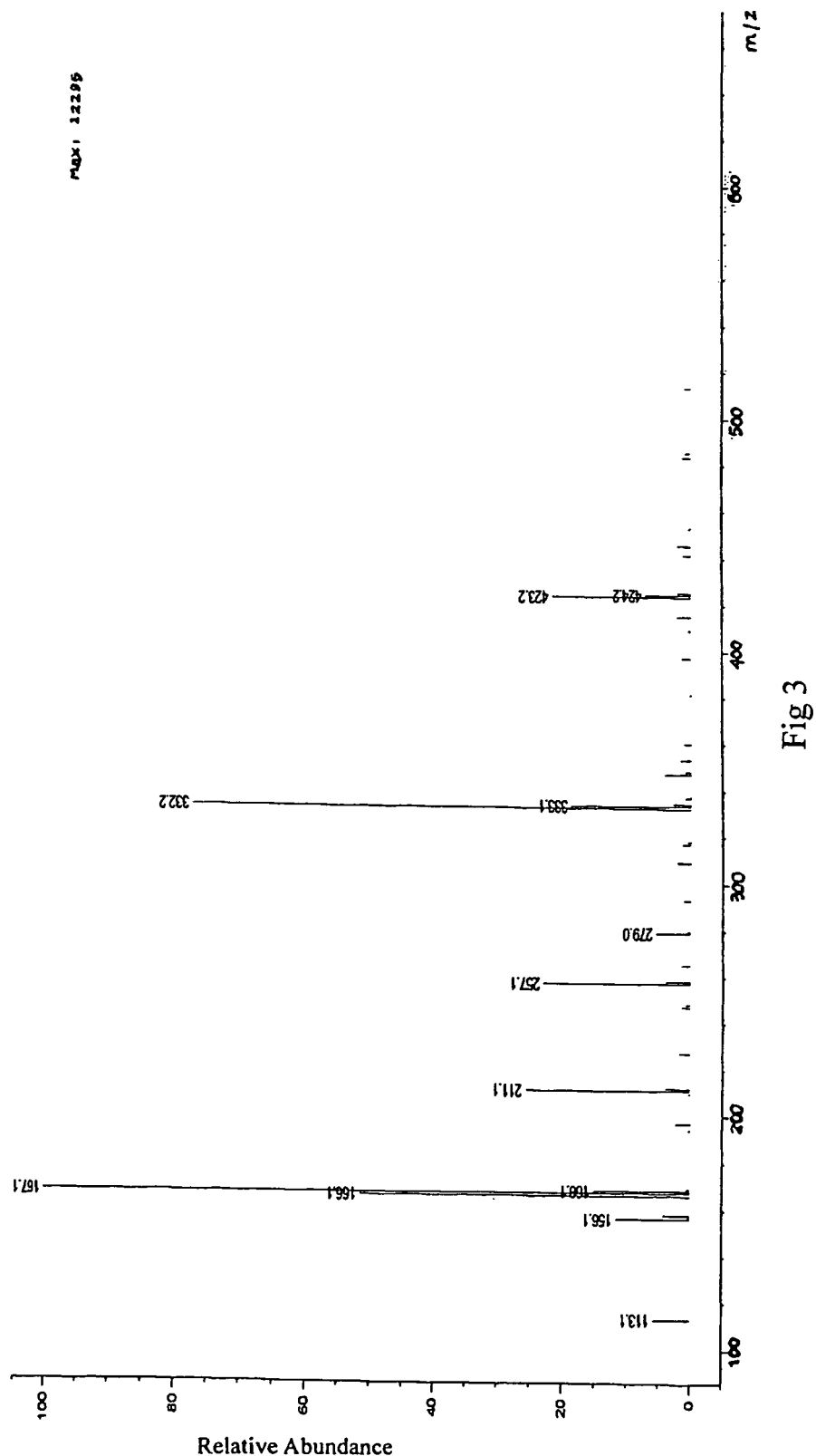
FIG. 3 is the Mass spectroscopy analysis of biphenyl acetate according to the above preferred embodiment of the present invention.

Mass spectroscopy analysis of biphenyl acetate is shown in FIG. 3.

The positive molecular ion ($C_{18}H_{23}NO_5$+·) of the biphenyl acetate molecule are examined that its charge-mass ratio (m/z) is 332.2 and relative abundance is 20. Therefore, the ratio value is 333.16 for calculating with accurate mass theory, because the low measuring accuracy of low resolution mass spectrometer generates mass relative error which is 5×10–4. In the theory, the calculating value of $C_{18}H_{22}NO_5$+ ion mass fragment is 332.15 m/z, so it only has 0.6×10–4 relative error.

The structure of the biphenyl acetic ammonia butantriol salt is I, and the purification is 99.5%.

The solution test of biphenyl acetic ammonia butantriol salt:

According to Chinese medicine book in 2005 edition, the preparation of biphenyl acetic ammonia butantriol salt is made by different solvent. In other words, they use acetone, formylamine, ethane nitrile, methanol, alcohol as the solvent to test their solubility. At first, mill the biphenyl acetic ammonia butantriol salt into flour and weight it, and add solvent into the biphenyl acetic ammonia butantriol salt. Second, at 25±2° C., wave the mixer solution every 5 minutes for 30 seconds, and inspect the dissolve situation. Repeat three times and the result is illustrated in Table 1. Referring to Table 1, the biphenyl acetic ammonia butantriol salt is dissolve with formamide, methanol, is just a few dissolve with water, and alcohol, and is undissolvable with acetone, and acetonitrile.

Preferred Embodiment 2

21.2 g (0.1 ml) of Biphenyl acetate, 12.1 g (0.1 mole) of ammonia butantriol, and 150 ml of absolute alcohol are added into a dry and clean 250 ml three opening round bottom crucible bottle. Stir the solution mixture at 50° C. 30 minutes for totally dissolving until the solution is in a clarified transparent manner. Evaporate the mixture solution and get white powder. Put the solution into vacuum dry machine at 80° C. Finally, we can get 32 grams of biphenyl acetic ammonia butantriol salt. The melting point thereof is between 163 and 164° C. The yield is 96.0%. The theoretical value of element analysis is C: 64.9%; H: 6.9%; N: 4.2%; O: 24%. The actual value of element analysis is C: 64.1%; H: 7.3%; N: 3.6%; O: 25%) The product is biphenyl acetic ammonia butantriol salt, and the purity is 99.2%.

Preferred Embodiment 3

21.2 g (0.1 ml) of Biphenyl acetate and 210 ml of benzene are added into a dry and clean 250 ml three opening round bottom crucible bottle. Stir and heat the mixture until the solution is perfect dissolved. Add ammonia butantriol into the mixture solution until the solution is in a clarified transparent manner. Stir the solution for two hours and make TLC fully reacting with the solution. Set the end point when the raw material biphenyl acetate is totally reacted with other reactants judge by TLC. Cool down to get huge amount of white crystal. Remove chloride and use absolute ether washing the white crystal and then put it into vacuum dry machine at 80° C. Finally, we can get the biphenyl acetic ammonia butantriol salt 28.5 grams. The melting point is between 163 and 164° C. The yield is 85.6%. The theoretical value of element analysis is C: 64.9%; H: 6.9%; N: 4.2%; O: 24%. The actual value of element analysis is C: 64.1%; H: 7.3%; N: 3.6%; O: 25%) The product is biphenyl acetic ammonia butantriol salt, and the purity is 99.8%.

Preferred Embodiment 4: Preparation of the Injection Liquid: Biphenyl Acetic Ammonia Butantriol Salt Recipe: 94 grams of biphenyl acetic ammonia butantriol salt and 1 to 2 grams of sodium carbonate to form 1000 syringes.

Use the method of preferred embodiment 1 to adjust the biphenyl acetic ammonia butantriol salt into a container, add a predetermined amount of water. Stir the mixture and meanwhile add 0.1% (0.1 g/100 ml) sodium carbonate until the biphenyl acetic ammonia butantriol salt is prefect dissolved. Control the pH value between 8.5 and 8.8. Add water up to 4000 ml. Add 2 gram of active carbon. Heat the solution for 15 minutes. Remove chloride and carbon from the solution. The liquid is filtered by 0.22 um micro filter, and is contained and sealed it to different syringe tubes. (Each tube includes 94 grams of biphenyl acetic ammonia butantriol salt). Finally, the solution is treated under a predetermined pressure and germ-free at 115° C. to form the final product.

Preferred Embodiment 5: Preparation of the Dry Powder of Biphenyl Acetic Ammonia Butantriol Salt to Form 1000 Dropper Bottles Recipe: 94 grams of biphenyl acetic ammonia butantriol salt and 20 grams of mannite.

Use the method of preferred embodiment 1 to adjust 94 grams of biphenyl acetic ammonia butantriol salt into a container, add 20 grams of mannite and a predetermined amount of water for solvent. Add water up to 3000 ml. Add 2 gram of active carbon. Heat the solution for 15 minutes. Remove chloride and carbon. The solution is filtered by 0.22 um micro filters, and is contained and sealed it to different dropper bottles. (each bottle includes 94 grams of biphenyl acetic ammonia butantriol salt).

Preferred Embodiment 6: Preparation of the Capsule of Biphenyl Acetic Ammonia Butantriol Salt Recipe: 188 grams of biphenyl acetic ammonia butantriol salt and 20 grams of lactose to form 1000 capsules.

Use the method of preferred embodiment 2 to adjust 94 grams of biphenyl acetic ammonia butantriol salt and go through 100 sieves. Add prescription lactose at 80° C. and go through 80 sieves, mixed, and test its component. Finally, fill it into the No. 1 capsule.

Preferred Embodiment 7: The Test of Medicine Effects of Biphenyl Acetic Ammonia Butantriol Salt 1. Pain Effects in a Mouse Injection Biphenyl Acetic Ammonia Butantriol Salt Pick the female Kunming mouse, each having the weight between 20 to 22 grams. At first, test their sensitive towards pain. Put the mouse on the hot plate with the temperature of 55±0.5° C., and calculate how much pain does the mouse has by determining how many times they lick their back leg. Eliminate the mice seem to like to jump and the mice has no respond for 30 seconds. Pick a total of 60 mice having sensitive to pain and divide them into 5 groups randomly. Use the method of preferred embodiment 4 to adjust the biphenyl acetic ammonia butantriol salt. The dosage of biphenyl acetic ammonia butantriol salt is divided into low, medium, and high dosage, correspondingly to 4, 12, 36 mg/kg, and normal dosage ⅓, 1, 3 respectively. And there is a positive contrast group. The mixture solution is injected into the vein of each of the mice according to its weight ratio 0.1 ml liquid/10 gram weight. On the other hand, the saline is injected into the vein in the contrast group. Use epilation to remove the hair of the back leg of the mouse. Record the painful of every mouse before giving drug, and record the painful after giving drug 1 hour. After the mouse licks its foot, remove the hot plate immediately. Do the same record again at the second and third hour after giving drug. Do the t inspect, and judge its effects on easing pain.

As shown in Table 2, it shows that the pain results are very similar on different mouse before giving drugs. After giving drugs, the biphenyl acetic ammonia butantriol salt is significantly extends the time which mouse is standing on the hot plate at first, second, and the third hour compared to the contrast group. In other words, it increases the ability of those mice to fight with pain.

2. The Pain Effects in a Kunming Mouse Injection Biphenyl Acetic Ammonia Butantriol Salt Towards Their Swelling Ears.

(1) Material and Recipe:
(1.1) Test Animals:
Kunming mouse: SPF LEVEL, male, 15-17 grams, a total numbers of 110 mice are used.
Certification number: SCXK 2003-0002, 2005A012
(1.2) Drugs: Use the Method of Preferred Embodiment 4 to Adjust the Biphenyl Acetic Ammonia Butantriol Salt
2. Methods and Results
Total numbers of 110 Kunming mice are used, male, 15-17 g, medical inspection for 3 days.

After testing, the mice are divided into eleven groups randomly and each group contains 10 mice. The numbers and dosage of the biphenyl acetic ammonia butantriol slat are 1, 2, 3, 4, 5 and 3, 6, 12, 24, 48, respectively. The numbers and dosage of flurbiprofen axetil are 1, 2, 3, 4, 5, and 3, 6, 12, 24, 48 respectively. Use the dimethybenzene to make the mouse ear swelling, and use the mouse left ear as the contrast group. After 30 minutes, the mixing liquid is injected into the vein according to its weight ratio 0.1 ml liquid/10 gram weight. Use a punch, having the diameter of 8 mm, to punch the same hole in two different ears. Weight it by very high quality scale. Finally, the swelling ratio is: the weight of right ear plus the weight of left ear.

Referring to Table 3, it shows the swelling ratio of the biphenyl acetic ammonia butantriol slat NO. 1, NO. 2, NO. 3, NO. 4, and NO. 5 and its swelling ratio caused by dimethybenzene respectively. (p lower than 0.05 and p higher than 0.01) On the same manner, the flurbiprofen axetil NO. 2, NO. 3, NO. 4, and NO. 5 is significantly reduces the swelling ratio towards Kunming mouse caused by dimethybenzene.

There is no significantly difference between biphenyl acetic ammonia butantriol and flurbiprofen axetil. To sum up, the effect of the biphenyl acetic ammonia butantriol towards the swelling ear caused by dimethybenzene is almost the same as the flurbiprofen axetil towards the swelling ear caused by dimethybenzene.

3. The Injection of Biphenyl Acetic Ammonia Butantriol Towards the NIH Mice Twisted Caused By the Acetic Acid.
1. Methods and Results
(1.1) Test Animals
NIH mice, SPF level, half of the mice are male and half of the mice are female, 15-17 g, a total numbers of 110 mice are used.
Certification number: SCXK 2003-0002, 2006A017
(1.2) Medicine
Use the method of preferred embodiment 4 to adjust the biphenyl acetic ammonia butantriol salt.

Flurbiprofen Axetil Injection Liquid
The Experiment Method and Result
After testing, the 110 NIH mice are divided into eleven groups randomly, which means each group has 10 mice, and each of the mice has a weight between 15 and 17 grams. The numbers and dosage of the biphenyl acetic ammonia butantriol slat are 1, 2, 3, 4, 5 and 3, 6, 12, 24, 48 mg/kg respectively. The numbers and dosage of flurbiprofen axetil are 1, 2, 3, 4, 5, and 3, 6, 12, 24, 48 respectively also. The medicine and weight ratio is 0.1 ml medicine/10 g weight. Meanwhile, we give the same quantity of saline solution to the contrast group. After 30 minutes, the mixture solution is injected into the vein according to its weight ratio 0.1 ml liquid/10 gram weight for HAc painful. Record the twist reaction every 15 minutes, count the twist reaction, and calculate the inhibition rate.

Table 4 shows the biphenyl acetic ammonia butantriol salt solution NOs. 1, 2, 3, 4, 5 and its control group can dramatically control the twist caused by the injection glacial acetic acid. ($P<0.05$ or $P>0.01$) ED 50 and 95% degree of confidence is 7.9 (4.7-13.5) mg/kg. Meanwhile, the flurbiprofen axetil solution NOs. 1, 2, 3, 4, 5 and its control group can dramatically control the twist caused by the injection glacial acetic acid. ($P<0.01$) ED 50 and 95% degree of confidence is 6.3 (4.9-6.3) mg/kg.

There is no significantly difference between biphenyl acetic ammonia butantriol and flurbiprofen axetil injection. To sum up, the effect of the biphenyl acetic ammonia butantriol towards the mouse twisted caused by glacial acetic acid is almost the same as the flurbiprofen axetil towards the mouse caused by glacial acetic acid.

Preferred Embodiment 8: the Safety Test of Injection of Biphenyl Acetic Ammonia Butantriol Salt The safety test is published by Chinese drug inspection department issued on August 2003. (GLP)
The Drug
(1) Use the Method of Preferred Embodiment 4 to Adjust the Biphenyl Acetic Ammonia Butantriol Salt
The initial dosage to the animal: vein injection, 94 mg/injection, use 0.9 % NACL solution dilates to 100-200 ml, once or twice injection per day.
(2) The Positive Contrast Group: White Egg, No: 050114
(3) The Positive Contrast Group: 0.9% (0.9g/100 ml) NACL Solution
2. Test Animal and Feed Condition:
Guinea Pig
a. level, race: the common level guinea pig.
b. Age: 10 to 12 weeks old.
c. First weight when purchasing/sex: 280-330 g, half of guinea pigs are male and half of guinea pigs are female.
d. original from, and evidence of certification: certification number: SCXK 2006-0015, 2006B-007.
e. animal pick explanation: guinea pig is one of the priority experiments for allergy test, it is recommended by the drug research guide.
f. Inspection procedure: do the investigation to the test animal before inspection. Review the appearance and behavior of the animal including defecation, food intake, and so on, and eliminate viral animal. The entire animal doing the investigation are required to have the permit from the investigation person.
g. Standard method: use the drying method, and use saturated sorrow and bitter solution to mark spot on different parts of animal for different number. Each group has 3 guinea pigs, and mark them respectively.
2. Rabbit
a. level, race: the common level rabbit.
b. Age: 3 months old.

c. First weight when purchasing, sex: 2.0-2.2 kg, half of the rabbits are male and half of the rabbits are female.

d. original from, and evidence of certification: certification number 2006A001 e. animal pick explanation: rabbit is one of the priority experiments of allergy test, it is recommended by the drug research guide.

f. Inspection procedure: the procedure is the same as guinea pig does.

g. Standard method: the method is the same as rabbit does. Feed the rabbits separately, and mark them.

(3) Feed Condition:

a. Feed management: the animal is feeding by people who own the certificate of feeding animal.

b. Feed condition, level, and certification: guinea pig and the rabbit are living in common guinea pig room and rabbit room respectively, all the utility meets the requirement of safety animal living, and good air ventilation and light, temperature is between 16-26° C., humidity is 40 to 70%; The animal safety certification number is: 2005C133. The test animal approval number is: SYXK-2003-0003 (ISSUED BY 2005).

c. Feed and drinking water: drinking water is the stuffs of feed.

Use the method of preferred embodiment 4 to adjust the biphenyl acetic ammonia butantriol salt and to do the safety experiment.

No. 1 the biphenyl acetic ammonia butantriol salt injection towards the guinea pig for the whole body allergy experiment 1. Method:

Take 24 experimental guinea pig, evenly divide into 4 groups by sex and weight randomly, each group has six male guinea pig and six female guinea pig. It divided into the positive contrast group, the negative contrast group, the low and high dosage group from the method of preferred embodiment 4 to adjust the biphenyl acetic ammonia butantriol salt, and it is 7.5 and 22.5 mg/kg bw equaling to one times and three times of the clinical usage respectively.

Injection through abdominal cavity, and the dosage per animal is 0.5 ml, for every other day for three sequence injections. Sensitizer dosage: the positive contrast group: NaCl solution is given (0.9 g/ml); the positive contrast group: 2% (2g/100 ml) white egg is given; the low dosage group: 7.5 mg the biphenyl acetic ammonia butantriol salt/kg bw. The high dosage group: 22.5 mg the biphenyl acetic ammonia butantriol salt/kg bw.

The concentration of medicine: the low dosage group: 5.0 mg biphenyl acetic ammonia butantriol salt/ml; the high dosage group: 15.0 mg biphenyl acetic ammonia butantriol salt/ml, wherein the method of making the high dosage solution is that use 1 bottle of biphenyl acetic ammonia butantriol salt solution (4 ml:94 mg/bottle) from the method of preferred embodiment 4. Take 4 ml the biphenyl acetic ammonia butantriol salt solution and dilute it with 0.9 % NACL solution to 6.3 ml. The concentration of the biphenyl acetic ammonia butantriol salt solution is: 15.0 mg the biphenyl acetic ammonia butantriol salt solution/ml solution). The method of making the low dosage solution is that use 1 bottle of biphenyl acetic ammonia butantriol salt solution (2 ml:15 mg/bottle) from the method of preferred embodiment 4. Take 2 ml the biphenyl acetic ammonia butantriol salt solution and dilute it with 0.9 % NaCl (0.9 g/100 ml) solution to 6.0 ml. The concentration of the biphenyl acetic ammonia butantriol salt solution is: 5.0 mg the biphenyl acetic ammonia butantriol salt solution/ml solution).

After 12 days of the cavity injection, the medicine is given by vein injection. medicine volume: 1.0 ml/per animal. Dosage: two times of allergy dosage. Inspection the animal responds.

2. Target of Investigation:

2.1 Allergy Period: Weigh the Animal Before Allergy, and Record the Animal Responds in Detail.

2.2 Allergic Reaction: Weight the Animal Before Exciting. Inspect the Animal Responds for 30 Minutes and Record in Table 5 in Detail.

3. Result:

We can judge the level of allergy and the reaction rate of allergy. If there is any animal having allergy after rejection, we can take two healthy guinea pigs to do the vein injection for medicine 2 ml. Do the Inspection of that are there any allergy situation caused by the feeding material.

4. Result:

4.1 Investigation in Normal Condition

In the period of investigation, the activity, the breath, and the stool examination of the guinea pigs have not showed significantly unusual. The weight change is shown in Table 7.

4.2 Active Allergic Reactions:

The allergic action and the active allergic towards the guinea pigs are shown in Table 8. There is no allergy symptom occurred in the negative control group. There is allergy symptom occurred in the positive control. The symptoms for six guinea pigs are hyperphea, polypena, step unstable, jumping, and death. There is no allergic symptom in low dosage reagent group and the high dosage reagent group.

The results show that there is no allergy symptom in the negative control group, but the entire guinea pigs of the positive control group went death. There is no allergic symptom in low dosage reagent group and the high dosage reagent group.

The results show that we use the method of preferred embodiment 4 to adjust the biphenyl acetic ammonia butantriol salt and do the whole body allergy test towards the guinea pig is negative effect.

2. The Blood Absorbing Test Towards the Biphenyl Acetic Ammonia Butantriol Salt

The blood absorbing test outside the body: put the biphenyl acetic ammonia butantriol salt making from the method of preferred embodiment 4 solution 0.63/mg/ml, 1.88 mg/ml into 2% red blood cell's suspending liquid, respectively. There is no blood absorbing reaction within 3 hours in each tube. The results show that we use the method of preferred embodiment 4 to adjust the biphenyl acetic ammonia butantriol salt and do the absorbing test outside the body towards the guinea pig is negative effect. The detail experimental methods and results are shown in the following:

The method of Making the Medicine:

(1) high dosage group: the high dosage group: use 1 bottle of biphenyl acetic ammonia butantriol salt solution (4 ml:94 mg/bottle) from the method of preferred embodiment 4. Take 0.5 ml the biphenyl acetic ammonia butantriol salt solution and dilute it with 0.9 % NaCl solution (0.9 g/100 ml) to 6.25 ml. The concentration of the biphenyl acetic ammonia butantriol salt solution is: 1.88 mg/the biphenyl acetic ammonia butantriol salt solution/ml solution).

(2) low dosage group: use 1 bottle of biphenyl acetic ammonia butantriol salt solution (4 ml:94 mg/bottle) from the method of preferred embodiment 4. Take 2 ml the biphenyl acetic ammonia butantriol salt solution and dilute it with 0.9 % NACL (0.9 g/100 ml) solution to 6.0 ml. The concentration of the biphenyl acetic ammonia butantriol salt solution is: 0.63 mg the biphenyl acetic ammonia butantriol salt solution/ml solution).

2. The Injection Method:

(1) the Preparation of 2% Red Blood Cell's Suspending Liquid

Take few milliliters of rabbit blood into a triangular flask and shake it for 10 minutes. Remove the fiber egg white, and get non-fiber blood. Separate the blood solution into few centrifuge tubes. Add ten times of 0.9% NaCl solution, well mixing, and centrifuge (1500 turns/minutes, 15 minutes) to remove the supernatant. Use 0.9% NaCl solution to wash the precipitation red blood two or three times until the supernatant is not red anymore. Use the red blood to mix the 0.9% NaCl solution to make 2% suspending liquid for test use.

Take the same size of opening of 7 clean test tubes and number them. Add the 0.9% NaCl solution, the injection water, medicine, and the 2% suspending liquid followed by Table 9. After well mixing, put them in the temperature chamber at 37° C. Inspect them every 15 minutes. After 1 hour, inspect them every one hour for 3 hours.

(2) Result Observation

If testing solution presents clearly red, no cellular residual under the tube, and few cellular residual, it can determines that haemolysis happens. If red cells all sink, and supernatant fluid presents no color, it can present that haemolysis doesn't happen. If there are red brown precipitates in the solution, and non-dispersed after shaking, it represents that the red cellular condensed matter happens. If red cellular coagulation happens, and further, it must be decide that it is true or faked coagulation. If condensed matters are uniform distribution after shaking the tube, it can be decided as faked coagulation. Or putting aggregate on this wave plate and put 2 drops 0.9% NaCl injection on the fringe of cap wave plate, and then observe in the scope, if red cellular condensed matter can be flushed scattering, it is faked coagulation. If condensed matter can not be flushed scattering, it is true coagulation.

3. Result Decision

While negative control tube has no haemolysis and coagulation, positive control tube has haemolysis, and the subject tube does not has haemolysis and coagulation in three hours, this sample (tested animal) can be used for injecting. If the subject tube has haemolysis and coagulation in three hours, this sample cannot be used for injecting.

4. The Results

After adding low concentration 0.63 mg/ml and high concentration 1.88 mg/ml the biphenyl acetic ammonia butantriol salt into different tubes, there is no blood absorbing reaction within 3 hours. In other words, the outside body blood test is negative effect as shown in Table 10 and Table 11.

The Blood Test of the Biphenyl Acetic Ammonia Butantriol Salt Injection Solution The Test of the Blood of Rabbit's Ear Pick 8 healthy rabbits; use the contrast method towards each right and left ear. Vein injection to the rabbit's left ear. The concentration of the medicine is 5 ml/kg weight. Use the method of preferred embodiment 4 to adjust the biphenyl acetic ammonia butantriol salt solution. The low dosage and high dosage of the biphenyl acetic ammonia butantriol salt solution is 3.15 mg/kg bw, and 9.4 mg/kg bw, respectively. Meanwhile the concentration of them is 0.63 mg/ml, and 1.88 mg/ml respectively which is 0.7-1.4 and 2-4 times of clinical vein injection. Vein injection to the rabbit's right ear for 0.9 g/100 ml NaCl is formed as the control group. Once a day, and repeats it for consecutive three days. After injection high and low dosage of solution, each rabbits is given 0.9% NACL liquid. Pick each two given high dosage and low dosage rabbits, and dissect it after 48 hours. Giving another two given high dosage and low dosage rabbits for two weeks recovery period, and then dissect it too. Finally, a sharp outline of a blood vessel, the thickness of rabbit's ear is even. There is no significant difference after using. There is no any poison on the animal's blood according to pathology. The method of preferred embodiment 4 to adjust the biphenyl acetic ammonia butantriol salt solution is conforming to the regulation standard.

The Method of the Experiment and the Result is Showing on the Following:

1. The Preparation of Test:

(1) High dosage group: use 2 bottles of biphenyl acetic ammonia butantriol salt solution (4 ml:94 mg/bottle) from the method of preferred embodiment 4. Take 8 ml the biphenyl acetic ammonia butantriol salt solution and dilute it with 0.9 % NaCl solution (0.9 g/100 ml) to 100 ml. The concentration of the biphenyl acetic ammonia butantriol salt solution is: 1.88 mg/the biphenyl acetic ammonia butantriol salt solution/ml solution).

(2) Low dosage group: take 30 ml of the above solution having concentration of 1.88 mg/ml. Take 30 ml of the biphenyl acetic ammonia butantriol salt solution and dilute it with 0.9 % NaCl (0.9 g/100 ml) solution to 90 ml. The concentration of the biphenyl acetic ammonia butantriol salt solution is: 0.63 mg the biphenyl acetic ammonia butantriol salt solution/ml solution).

2. Weight the Animal: Weight the Animal Before Injection, and After Injection for 48 Hours and 14 Days.

3. Regular Inspection and Animal Pick

Observe and record the response of the animal every day before injection every day. After the final injection for 48 hours, the high concentration and the low concentration rabbits are being killed by bleeding. Record the blood reaction. Cut the left ear first, and then cut the right ear from the boundary part of the ear, and then mark it. Cut a portion of the ears sample into 10% methylene liquid. The sample is 8 cm in length, and 1 cm in width, wherein a first cut is formed at 0.5 cm from the first needle point, a second cut is formed at 2 cm from the third needle point, and the thread side is the second cut. On the other hand, after 14 days of giving medicine, the high and low dosage animals do the following inspection. Use the first needle point as the boundary, cut one section from the first cut. And use the third needle point as boundary, cut two sections from the second cut. Use paraffin to form the sampling slice. The thickness of sampling slice is between 4 and 5 μm. The sampling slice is treated by H-E dying for inspection.

4. Judge the Results

Do the comprehensive judge by visual examination and inspection.

5. The Results 5.1 Visual Examination:

Obverse and record the response of the animals every day before injection. Between the drugs given periods, we can see the skin of the rabbit's ear for the high concentration and low concentration is red. The size is between 0.1×0.2 and 0.2×1.0 cm. After 48 hours of final injection, the investigation of four rabbits of high concentration and low concentration: a sharp outline of a blood vessel, the thickness of rabbit's ear is even. There is no significant difference after using as shown in Table 12 and Table 13. After 14 days of final injection, the investigation of four rabbits of high concentration and low concentration: a sharp outline of a blood vessel, the thickness of rabbit's ear is even. There is no significant difference after using.

5.2 The Investigation:

After 48 hours of giving high and low dosages of the biphenyl acetic ammonia butantriol salt solution, we dissect the rabbits. On the same method, after two weeks of giving high and low dosages of the biphenyl acetic ammonia butantriol salt solution, we dissect the rabbits. There is no degenerate and necrosis on the structure of the blood.

The Muscle Test of the Biphenyl Acetic Ammonia Butantriol Salt Solution

Pick 8 healthy rabbits; use the contrast method towards rabbit's muscle. Vein injection to the rabbit's left muscle once a day for 3 days. The concentration of the medicine is 1 ml/kg weight. Use the method of preferred embodiment 4 to adjust the biphenyl acetic ammonia butantriol salt solution. The concentration of low dosage and high dosage of the biphenyl acetic ammonia butantriol salt solution is 0.63 mg/ml, and 1.88 mg/ml respectively which is 0.7-1.4 and 2-4 times of clinical vein injection. Vein injection to the rabbit's right muscle for 0.9g/100 ml NACL is set as the control group. After injection of high and low dosages of solution, each rabbits is given 0.9% NaCl liquid. Pick each two given high dosage and low dosage rabbits, and dissect it after 48 hours. Giving another two given high dosage and low dosage rabbits two weeks recovery period, and then dissect them too. Do the visual inspection of eight rabbits: the muscular tissue around injection is full of flexibility and luster, no significant change. There is no degenerate and necrosis on the structure of the deep muscle of the rabbit according to pathology. The method of preferred embodiment 4 to adjust the biphenyl acetic ammonia butantriol salt solution is conforming to the regulation standard.

The Method of the Experiment and the Result is Showing on the Following:

1. The preparation of Test:

(1) High dosage group: use 1 bottle of biphenyl acetic ammonia butantriol salt solution (4 ml:94 mg/bottle) from the method of preferred embodiment 4. Take 1 ml the biphenyl acetic ammonia butantriol salt solution and dilute it with 0.9% NaCl solution (0.9 g/100 ml) to 12.5 ml. The concentration of the biphenyl acetic ammonia butantriol salt solution is: 1.88 mg/the biphenyl acetic ammonia butantriol salt solution/ml solution).

(2) Low dosage group: take 2 ml of the above solution having concentration 1.88 mg/ml. Take 2 ml the biphenyl acetic ammonia butantriol salt solution and dilute it with 0.9% NaCl (0.9 g/100 ml) solution to 6 ml. The concentration of the biphenyl acetic ammonia butantriol salt solution is: 0.63 mg the biphenyl acetic ammonia butantriol salt solution/ml solution).

2. Weight the Animal: Weight the Animal Before Injection, and After Injection for 48 Hours and 14 Days.

3. The Injection Method

Pick 8 healthy white rabbits. Inject high dosage and low dosage biphenyl acetic ammonia butantriol salt solutions into left muscle using aseptic method. On the contrary, inject the same volume 0.9% NaCl into the right muscle as the contrast group.

4. Regular Inspection

Observe and record the injection portions around the muscle portions of the animals every day before injection. After the final injection for 48 hours, the high concentration and the low concentration rabbits are being killed by bloodletting, and expose the muscle. Cut it through longitudinal direction. Record the injection portion by visual examination. On the other hand, after 14 days of giving medicine, two rabbits were given by the high and low dosage medicine animal do the inspection around the injection portion.

5. Judge the Results

Do the comprehensive judge by visual examination and inspection.

6. The Results

The result is shown in the Table 14, Table 15, Table 16, Table 17, and the diagnosis report.

After 48 hours and 14 days of giving high and low dosage of the biphenyl acetic ammonia butantriol salt solution, we do the visual examination and read the report: After using the biphenyl acetic ammonia butantriol salt solution on the rabbit's muscle portion, there is no degenerate and necrosis on the structure of the muscle portion.

The results show that we use the method of preferred embodiment 4 to adjust the biphenyl acetic ammonia butantriol salt (7.5/22.5 mg/kg bw) and do the whole body allergy test towards the guinea pig is negative effect. The results show that we use the method of preferred embodiment 4 to adjust the biphenyl acetic ammonia butantriol salt 0.63/1.88 mg/ml) and do the inspection towards the rabble's ear boundary is negative effect. The results show that we use the method of preferred embodiment 4 to adjust the biphenyl acetic ammonia butantriol salt 0.63/1.88 mg/ml) and do the inspection towards the rabbit for outside body blood absorption is negative effect.

Preferred Embodiment 9: The Poison Test Towards the Mouse for the Biphenyl Acetic Ammonia Butantriol Salt We can not judge the effects of the biphenyl acetic ammonia butantriol salt injection towards the NIH mice (half mousse are died) Therefore, we use the maximum dosage of the biphenyl acetic ammonia butantriol salt injection towards the NIH mice to do the research about the poison of the biphenyl acetic ammonia butantriol salt towards the NIH mice.

A total amount of 40 NIH mice, 19-21 gram, (half of the mice are male and half of the mice are female), it is divided into two groups: medicine group and the contrast group. The medicine is given by the maximum dosage of the biphenyl acetic ammonia butantriol salt (94 mg/4 ml) medicine volume: 0.2 ml/once/10 g weight), twice a day, two injections are six hours difference, i.e. the total dosage for one day is 940 mg/kg. The contrast is given by the 0.1% NaCl liquid. Investigation and record the poison effect on the mice and the amount of mice death. The result is that the entire mice in the medicine group are barely to move. Some mice are very hard to breath. After injection for 2 to 4 hours, the condition of the entire mice is getting better. The entire condition of the mice in the contrast group is normal. After injection for 14 days, no mouse went death in both group, and they look good for gaining weight. And dissect all of them; there is no significantly change by visual examination. The research show that the maximum enduring quantity of the NIH mice towards the biphenyl acetic ammonia butantriol salt is over 940 mg/kg. (calculated for the enduring quantity for biphenyl acetic ammonia is 598 mg/ml) Meanwhile biphenyl acetic acid ester for vein injection LD50 is 337 mg/ml for male, and 433 mg/ml for female. The position of the biphenyl acetic ammonia butantriol is significantly decreased, and its poison is also lower than other anti-inflammatory agent.

Preferred Embodiment 10: the Stable Test of the Biphenyl Acetic Ammonia Butantriol Salt Injection According to the Chinese pharmacopia appendix XI X C, second edition, 2005 (the rule of medicine stability testing direction), Committing the implement sample 4 of the stability investigation item for biphenyl acetic ammonia butantriol salt injection includes the influence factors testing (includes high temperature, high humidity, and highlights), accelerating testing, long term testing and so on. The purpose is to investigate the regular change of this product which has the influence of temperature, humidity, and light intensity, and offer producing, packaging, and transporting condition for this medicine. At the same time, the effective date is established by passing this testing. According to the Chinese pharmacopia appendix XI X C, second edition, 2005(the rule of medicine stability testing direction) and "The important stability item-list of bulk drug and pharmaceutical preparation" which is in "The researching directive rule of chemical medicine and therapeutic biological products" determines the important item-list, which includes gender character, PH value, relative materials, asepsis, thermal source, assay, and so on. The testing result is below:

1. Influence Test:

After putting the biphenyl acetic ammonia butantriol salt at high temperature 60° C., high humidity (relative humidity 92.5±5%), and light intensity (4500±500lx) for 10 days, there is no significantly change for the product in different standard evolution. In other words, the quality of the product is very stable.

2. Acceleration Test

After putting the biphenyl acetic ammonia butantriol salt at high temperature 40±2° C., high humidity (relative humidity 75±5%), and for 3 months, there is no significantly change for the product in every month examination. In other words, the quality of the product is very stable.

3. Long Term Test

After putting the biphenyl acetic ammonia butantriol salt at high temperature 25° C., high humidity (relative humidity 25%) for 3 months, there is no significantly change for the product in every month examination. In other words, the quality of the product is very stable.

Preferred Embodiment 11: the Test of Stomach Channel Towards the Biphenyl Acetic Ammonia Butantriol Salt Oral Administration NIH mice are divided into two groups randomly. After fasting for 24 hours, the NIH mice are fed by 333 mg/kg of the biphenyl acetic ammonia butantriol salt, and 212 mg/kg of the biphenyl acetic. Dissect stomach after 48 hours. Use 10% methylene oxide. Cut the stomach along the curve of stomach, and calculate the percentage of an ulcer canker. The result is shown in Table 18.

Industry Application

The biphenyl acetic ammonia butantriol salt of the present invention can dissolve in water, so this benefit can solve the problem of incapable of dissolving the biphenyl phenylacetic acid in water. At the same time of solving the solubility problem, the present invention proves the analgesic and anti-inflammatory equivalence of biphenyl acetic ammonia butantriol salt and biphenyl phenylacetic ester. In addition, we can know the result is that biphenyl acetic ammonia butantriol salt has the lower acute toxicity than biphenyl phenylacetic ester (see Example 9), and lower oral irritation (see Example 11). On this basis, we go a step further to do the allergic reactive experiment which follows the GLP testing rule, and finally, we don't find the allergic reaction and shocking phenomena which cause from allergy. At the same time, according to a normal injection requirement, we did the haemolysis and irritating testing of biphenyl acetic ammonia butantriol salt, and than we found that there is no irritation of haemolysis, muscle, and blood vessel, so it can use for injection.

All of the above experiment proceeds in the national new medicine safety evaluation pharmacy research important laboratory, so the data have the high reliability. This medicine can be used for injection, and avoid to use big molecular coemulsifier of producing emulsion. If we want to use biphenyl phenylacetic ester for emulsion, stability is the big problem for pharmaceutics workers, such as acidification. The present invention does a three months stability testing of biphenyl acetic ammonia butantriol salt injection, and we find that biphenyl acetic ammonia butantriol salt injection has high stability. The procedure of producing emulsion is restaining, but the procedure of producing biphenyl acetic ammonia butantriol salt and coemulsifier is easy to proceed.

The manufacturing technique of biphenyl acetic ammonia butantriol salt is very easy to proceed. The raw material is very easy to find, and the reaction is stability, high yield, and the product purity is high. So, we can directly to get the medical biphenyl acetic ammonia butantriol salt. In addition, there is no serious environmental pollutant in this producing procedure. According to the pharmaceutical testing, it can be proved that biphenyl acetic ammonia butantriol salt injection has the influence to ease analgesic, anti-inflammatory, and no allergy for mice.

For the external testing, there is no red blood cell haemolysis influence on Japan big ears' rabbit. Because of no obviously irritant influence on giving many times and one time of medicine to rabbits' vein vessel and muscle, it explain that biphenyl acetic ammonia butantriol salt can apply to muscle and vein injection. After giving one time medicine to rabbits' vein, the result of acute toxicity testing reveals that the tolerance value of NIH mice in injecting biphenyl acetic ammonia butantriol salt is 940 mg/kg. This result reveals the LD50 value of biphenyl acetic ammonia butantriol salt is higher than 940 mg/kg (biphenyl phenylacetic acid is 589 mg/kg), but the LD50 value of biphenyl phenylacetic ester is 337 mg/kg for male and 433 mg/kg for female. The acute toxicity of biphenyl acetic ammonia butantriol salt dramatically decreases, and its acute toxicity is lower than the same kinds of anti-inflammatory and analgesics medicines. Biphenyl acetic ammonia butantriol salt has the lower irritant of stomach, intestine, mouth, and abdomen than biphenyl phenylacetic acid, and further easy to take this medicine.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

TABLE 1

| | | the solubility testing | | | |
|---|---|---|---|---|---|
| Solute | Solvent | The amount of biphenyl acetic ammonia butantriol salt (g) | The amount of solvent (ml) | The dissolving condition | Conclusion |
| The amount of biphenyl acetic ammonia butantriol salt | Methanol | 0.1135 | 3 | Completely dissolved | Dissolved |
| | Water | 14.1 | 10 | Completely dissolved | Slightly dissolved |

TABLE 1-continued the solubility testing

| Solute | Solvent | The amount of biphenyl acetic ammonia butantriol salt (g) | The amount of solvent (ml) | The dissolving condition | Conclusion |
|---|---|---|---|---|---|
| | Alcohol | 14.3 | 10 | Completely dissolved | Slightly dissolved |
| | Acetone | 8.9 | 150 | Completely dissolved | Undissolvable or almost undissolvable |
| | Acetonitrile | 9.1 | 150 | Completely dissolved | Undissolvable or almost undissolvable |
| | Formamide | 0.2137 | 6 | Completely dissolved | Dissolved |

TABLE 2

| Group | The number of animals (amount) | Dosage (mg/kg) | | 1 hour | 2 hours | 3 hours |
|---|---|---|---|---|---|---|
| The blank control group | 12 | — | | 19.15 ± 2.97 | 20.18 ± 2.97 | 20.24 ± 3.16 | 20.43 ± 2.85 |
| Low dose group | 12 | 4 | | 19.38 ± 2.96 | 25.16 ± 5.67 | 23.00 ± 2.79 | 22.25 ± 3.16 |
| Medium dose group | 12 | 12 | | 20.24 ± 2.56 | 33.50 ± 5.54** | 32.12 ± 2.95** | 30.75 ± 3.15** |
| High dose group | 12 | 36 | | 19.76 ± 3.74 | 39.83 ± 4.15*** | 34.65 ± 3.84*** | 33.58 ± 2.15*** |
| Lysine Acetyl-salicylate | 12 | 240 | | 19.15 ± 3.46 | 31.08 ± 4.26** | 30.35 ± 3.29** | 28.16 ± 2.97** |

*P < 0.05,
**P < 0.01
analgesia affection of mice heating plate method's for injecting the biphenyl acetic ammonia butantriol salt liquid.

TABLE 3 the affection of expansion in Kunming mouse for biphenyl acetic ammonia butantriol salt injection in dimethyl benzene

| Group | | Dosage (mg/kg) | The number of animals (amount) | Degree of expansion (mg) |
|---|---|---|---|---|
| Model group | | — | 10 | 17.1 ± 3.8 |
| Biphenyl acetic ammonia butantriol salt injection | No. 1 | 3 | 10 | 13.9 ± 2.6* |
| | No. 2 | 6 | 10 | 13.5 ± 2.9* |
| | No. 3 | 12 | 10 | 13.0 ± 2.7* |
| | No. 4 | 24 | 10 | 12.7 ± 2.9* |
| | No. 5 | 18 | 10 | 10.9 ± 2.5** |
| Flurbiprofen Axetil | No. 1 | 3 | 10 | 14.2 ± 2.7* |
| | No. 2 | 6 | 10 | 13.2 ± 3.6** |
| injection | No. 3 | 12 | 10 | 11.7 ± 3.6** |
| | No. 4 | 24 | 10 | 11.4 ± 4.7** |
| | No. 5 | 48 | 10 | 10.9 ± 3.3** |

Compare with model group:
*p < 0.05,
**p < 0.01

TABLE 4

| Group | | Dosage Dose (mg/kg) | The number of animals (amount) | The number of twist (times) | Inhibitory rate (%) | ED50 and 95% degree of confidence |
|---|---|---|---|---|---|---|
| Model group | | — | 10 | 19.9 ± 5.9 | — | — |
| Biphenyl acetic ammonia butantriol salt injection | No.1 | 3 | 10 | 13.2 ± 5.5* | 33.7 | 7.9 mg/kg |
| | No.2 | 6 | 10 | 11.5 ± 5.4** | 42.2 | (4.7-13.5) |
| | No.3 | 12 | 10 | 7.1 ± 3.4** | 64.3 | |
| | No.4 | 24 | 10 | 6.8 ± 3.0** | 65.8 | |
| | No.5 | 48 | 10 | 5.1 ± 3.0** | 74.4 | |
| Flurbiprofen | No.1 | 3 | 10 | 12.7 ± 4.8** | 36.2 | 6.3 mg/kg |

TABLE 4-continued

| Group | | Dosage Dose (mg/kg) | The number of animals (amount) | The number of twist (times) | Inhibitory rate (%) | ED50 and 95% degree of confidence |
|---|---|---|---|---|---|---|
| Axetil injection | No.2 | 6 | 10 | 9.6 ± 3.0** | 51.8 | (4.3-9.3) |
| | No.3 | 12 | 10 | 7.4 ± 3.7** | 62.8 | |
| | No.4 | 24 | 10 | 6.5 ± 2.6** | 66.8 | |
| | No.5 | 48 | 10 | 4.4 ± 3.2** | 77.9 | |

Compare with model group: *p < 0.05, **p < 0.01
the affection of expansion in Kunming mouse for biphenyl acetic ammonia butantriol salt injection glacial acetic acid

TABLE 5 allergic reaction symptom
Allergic reaction

| 0 | Normal |
|---|---|
| 1 | Mania |
| 2 | Piloerection |
| 3 | Shivering |
| 4 | Itching mouse |
| 5 | Sneezing |
| 6 | Coughing |
| 7 | Hyperphea |
| 8 | Micturate |
| 9 | Defecation |
| 10 | Lacrimation |
| 11 | Dyspnea |
| 12 | Voar |
| 13 | Peliosis |
| 14 | Step unstable |
| 15 | Jumping |
| 16 | Polypona |
| 17 | Spasm |
| 18 | Spin |
| 19 | Respiration cheyne |
| 20 | Death |

TABLE 6 allergenicity evaluation
standard of *cavia porcellus*

| Reaction symptom | Evaluation standard |
|---|---|
| 0 | Allergic reaction negative (−) |
| 1-4 | Allergic reaction weak positive (+) |
| 5-10 | Allergic reaction positive (++) |
| 11-19 | Allergic reaction strong positive (+++) |
| 20 | Allergic reaction extremely strong positive (++++) |

TABLE 7

| Group | Animals' number | Gender | Weight (g) D1 | D5 | D17 | D17 weight change (g) |
|---|---|---|---|---|---|---|
| Negative control group | 1 | ♀ | 332 | 342 | 395 | 63 |
| | 3 | ♀ | 355 | 360 | 422 | 67 |
| | 6 | ♀ | 323 | 337 | 344 | 21 |
| | 7 | ♂ | 345 | 366 | 428 | 83 |
| | 8 | ♂ | 301 | 310 | 363 | 62 |
| | 12 | ♂ | 348 | 344 | 412 | 64 |
| | Average value | | 334 | 343 | 394 | 60 |
| | SD | | 20 | 20 | 34 | 21 |
| Positive control group | 2 | ♀ | 347 | 348 | 405 | 58 |
| | 10 | ♀ | 315 | 319 | 355 | 40 |
| | 12 | ♀ | 334 | 283 | 340 | 6 |
| | 1 | ♂ | 320 | 328 | 367 | 47 |

TABLE 7-continued

| Group | Animals' number | Gender | Weight (g) D1 | D5 | D17 | D17 weight change (g) |
|---|---|---|---|---|---|---|
| | 2 | ♂ | 310 | 334 | 380 | 70 |
| | 9 | ♂ | 360 | 372 | 418 | 58 |
| | Average value | | 331 | 331 | 378 | 47 |
| | SD | | 20 | 30 | 30 | 22 |
| Given medicine group (7.5 mg/kg · bw) | 5 | ♀ | 330 | 333 | 352 | 22 |
| | 7 | ♀ | 335 | 349 | 406 | 71 |
| | 8 | ♀ | 337 | 327 | 376 | 39 |
| | 6 | ♂ | 318 | 358 | 380 | 62 |
| | 10 | ♂ | 351 | 367 | 427 | 76 |
| | 11 | ♂ | 329 | 330 | 366 | 37 |
| | Average value | | 333 | 344 | 385 | 51 |
| | SD | | 11 | 16 | 27 | 22 |
| Given medicine group (22.5 mg/kg · bw) | 4 | ♀ | 338 | 347 | 356 | 18 |
| | 9 | ♀ | 331 | 307 | 318 | −13 |
| | 11 | ♀ | 333 | 328 | 448 | 115 |
| | 3 | ♂ | 332 | 324 | 283 | −49 |
| | 4 | ♂ | 351 | 338 | 375 | 15 |
| | 5 | ♂ | 315 | 294 | 312 | 56 |
| | Average value | | 333 | 323 | 349 | 24 |
| | SD | | 12 | 20 | 59 | 57 | the active allergic testing of animals' change condition in cavia porcellus for the biphenyl acetic ammonia butantriol salt injection.
1. D1, D5 and D17 represents as first time allergy, last time allergy, and the weight at the allergy day.
2. D17 the weight change is equal to D17-D1, positive number means gain weight

TABLE 8 allergic reaction condition of the whole body active
allergic testing in injecting the biphenyl acetic ammonia
butantriol salt injection. Allergic reaction incidence rate =
(numbers of allergy animals ÷ total numbers of animals) × 100%

| Group | Animals' number | Reaction symptom | Reaction's degree or times | Allergic reaction incidence rate (%) |
|---|---|---|---|---|
| Negative control group | 1 | − | − | 0 |
| | 3 | − | − | |
| | 6 | − | − | |
| | 7 | − | − | |
| | 8 | − | − | |
| | 12 | − | − | |
| Positive control group | 2 | Died | ++++ | 100 |
| | 10 | Died | ++++ | |
| | 12 | Died | ++++ | |
| | 1 | Died | ++++ | |
| | 2 | Died | ++++ | |
| | 9 | Died | ++++ | |
| Reagent group (7.5 mg/ kg · bw) | 5 | − | − | 0 |
| | 7 | − | − | |
| | 8 | − | − | |
| | 6 | − | − | |
| | 10 | − | − | |
| | 11 | − | − | |

TABLE 8-continued allergic reaction condition of the whole body active
allergic testing in injecting the biphenyl acetic ammonia
butantriol salt injection. Allergic reaction incidence rate =
(numbers of allergy animals ÷ total numbers of animals) × 100%

| Group | Animals' number | Reaction symptom | Reaction's degree or times | Allergic reaction incidence rate (%) |
|---|---|---|---|---|
| Reagent Group (22.5 mg/ kg · bw) | 4 | – | – | 0 |
| | 9 | – | – | |
| | 11 | – | – | |
| | 3 | – | – | |
| | 4 | – | – | |
| | 5 | – | – | |

TABLE 9

| ml | Test Tube's number | | | | | | |
|---|---|---|---|---|---|---|---|
| | 1 | 2 | 3 | 4 | 5 | 6 | 7 |
| 2% red blood cell's suspending liquid | 2.5 | 2.5 | 2.5 | 2.5 | 2.5 | 2.5 | 2.5 |
| 0.9% NaCl injection | 2.0 | 2.1 | 2.2 | 2.3 | 2.4 | 2.5 | — |
| Injecting water | — | — | — | — | — | — | 2.5 |
| Solution sample | 0.5 | 0.4 | 0.3 | 0.2 | 0.1 | — | — | number of 2% red blood cell's suspending liquid

TABLE 10

| Test liquid (ml) | Tube's number | | | | | | |
|---|---|---|---|---|---|---|---|
| | 1 | 2 | 3 | 4 | 5 | 6 | 7 |
| 2% red blood cell's suspending liquid | 2.5 | 2.5 | 2.5 | 2.5 | 2.5 | 2.5 | 2.5 |
| 0.9% NaCl injection (ml) | 2.0 | 2.1 | 2.2 | 2.3 | 2.4 | 2.5 | 0.0 |
| Injecting water (ml) | 0.0 | 0.0 | 0.0 | 0.0 | 0.0 | 0.0 | 2.5 |
| The biphenyl acetic ammonia butantriol salt injection (high amount) (ml) | 0.5 | 0.4 | 0.3 | 0.2 | 0.1 | 0.0 | 0.0 |
| Judging conclusion The conclusion of keeping warm at 37° C. after 15 minutes | – | – | – | – | – | – | + |
| The conclusion of keeping warm at 37° C. after 30 minutes | – | – | – | – | – | – | + |
| The conclusion of keeping warm at 37° C. after 45 minutes | – | – | – | – | – | – | + |
| The conclusion of keeping warm at 37° C. after 1 hour | – | – | – | – | – | – | + |
| The conclusion of keeping warm at 37° C. after 2 hours | – | – | – | – | – | – | + |
| The conclusion of keeping warm at 37° C. after 3 hours | – | – | – | – | – | – | + | result of hemolytic testing (application of visual) of the biphenyl acetic ammonia butantriol salt injection (high dosage) (ml). ps.
"+" means absolutely dissolved,
"–" means insolubility, and tube 6 is the negative contrast group tube.
Tube 7 is the positive contrast group tube.

TABLE 11

| Test liquid (ml) | Tube's number | | | | | | |
|---|---|---|---|---|---|---|---|
| | 1 | 2 | 3 | 4 | 5 | 6 | 7 |
| 2% red blood cell's suspending liquid | 2.5 | 2.5 | 2.5 | 2.5 | 2.5 | 2.5 | 2.5 |
| 0.9% NaCl injection (ml) | 2.0 | 2.1 | 2.2 | 2.3 | 2.4 | 2.5 | 0.0 |
| Injecting water (ml) | 0.0 | 0.0 | 0.0 | 0.0 | 0.0 | 0.0 | 2.5 |
| The biphenyl acetic ammonia butantriol salt injection (high amount) (ml) | 0.5 | 0.4 | 0.3 | 0.2 | 0.1 | 0.0 | 0.0 |
| Judging conclusion The conclusion of keeping warm at 37° C. after 15 minutes | – | – | – | – | – | – | + |
| The conclusion of keeping warm at 37° C. after 30 minutes | – | – | – | – | – | – | + |
| The conclusion of keeping warm at 37° C. after 45 minutes | – | – | – | – | – | – | + |
| The conclusion of keeping warm at 37° C. after 1 hour | – | – | – | – | – | – | + |
| The conclusion of keeping warm at 37° C. after 2 hours | – | – | – | – | – | – | + |
| The conclusion of keeping warm at 37° C. after 3 hours | – | – | – | – | – | – | + | the result of hemolytic testing (application of visual) of the biphenyl acetic ammonia butantriol salt injection (low dosage) (ml). ps.
"+" means absolutely dissolved,
"–" means insolubility, and tube 6 is the negative contrast group tube.
Tube 7 is the positive contrast group tube.

TABLE 12 the exciting reaction of rabbits' ear for the biphenyl
acetic ammonia butantriol salt injection (Application of
visual inspection after 48 hours regent time) (high dosage)

| Rabbits No. | Left ear (reagent side) | Right ear (the control group side) |
|---|---|---|
| 1 | A sharp outline of a blood vessel, the thickness of rabbit's ear is even. There is no significant difference after using. | A sharp outline of a blood vessel, the thickness of rabbit's ear is even. There is no significant difference after using. |
| 3 | The skin color of injection area is red (0.1 cm × 0.5 cm). A sharp outline of a blood vessel, the thickness of rabbit's ear is even. There is no significant difference after using. | A sharp outline of a blood vessel, the thickness of rabbit's ear is even. There is no significant difference after using. |
| 4 | A sharp outline of a blood vessel, the thickness of rabbit's ear is even. There is no significant difference after using. | The skin color of injection area is red (0.2 cm × 0.5 cm). A sharp outline of a blood vessel, the thickness of rabbit's ear is even. There is no significant difference after using. |

TABLE 12-continued the exciting reaction of rabbits' ear for the biphenyl
acetic ammonia butantriol salt injection (Application of
visual inspection after 48 hours regent time) (high dosage)

| Rabbits No. | Left ear (reagent side) | Right ear (the control group side) |
|---|---|---|
| 6 | A sharp outline of a blood vessel, the thickness of rabbit's ear is even. There is no significant difference after using. | A sharp outline of a blood vessel, the thickness of rabbit's ear is even. There is no significant difference after using. |

TABLE 13 the exciting reaction of rabbits' ear for the biphenyl
acetic ammonia butantriol salt injection (Application of
visual inspection after 48 hours regent time) (low dosage)

| Rabbits No. | Left ear (reagent side) | Right ear (the control group side) |
|---|---|---|
| 2 | A sharp outline of a blood vessel, the thickness of rabbit's ear is even. There is no significant difference after using. | A sharp outline of a blood vessel, the thickness of rabbit's ear is even. There is no significant difference after using. |
| 5 | The skin color of injection area is red (0.1 cm × 0.2 cm). A sharp outline of a blood vessel, the thickness of rabbit's ear is even. There is no significant difference after using. | A sharp outline of a blood vessel, the thickness of rabbit's ear is even. There is no significant difference after using. |
| 7 | The skin color of injection area is red (0.1 cm × 0.2 cm). A sharp outline of a blood vessel, the thickness of rabbit's ear is even. There is no significant difference after using. | A sharp outline of a blood vessel, the thickness of rabbit's ear is even. There is no significant difference after using. |
| 8 | The skin color of injection area is red (0.1 cm × 0.2 cm). A sharp outline of a blood vessel, the thickness of rabbit's ear is even. There is no significant difference after using. | A sharp outline of a blood vessel, the thickness of rabbit's ear is even. There is no significant difference after using. |

TABLE 14 the exciting reaction of rabbits' muscle
(Application of visual) for the biphenyl acetic
ammonia butantriol salt injection (high dosage)

| Animal No. | Left leg quadriceps muscle (reagent side) | Right leg quadriceps muscle (control side) |
|---|---|---|
| 1 | The muscular tissue around injection area is full of flexibility and luster, no significant change | The muscular tissue around injection area is full of flexibility and luster, no significant change |
| 3 | The muscular tissue around injection area is full of flexibility and luster, no significant change | The muscular tissue around injection area is full of flexibility and luster, no significant change |
| 4 | The muscular tissue around injection area is full of flexibility and luster, no significant change | The muscular tissue around injection area is full of flexibility and luster, no significant change |
| 6 | The muscular tissue around injection area is full of flexibility and luster, no significant change | The muscular tissue around injection area is full of flexibility and luster, no significant change |

TABLE 15 the exciting reaction of rabbits'
muscle (Application of visual) for the biphenyl
acetic ammonia butantriol salt injection (low dosage)

| Animal No. | Left leg quadriceps muscle (reagent side) | Right leg quadriceps muscle (control side) |
|---|---|---|
| 2 | The muscular tissue around injection area is full of flexibility and luster, no significant change | The muscular tissue around injection area is full of flexibility and luster, no significant change |
| 5 | The muscular tissue around injection area is full of flexibility and luster, no significant change | The muscular tissue around injection area is full of flexibility and luster, no significant change |
| 7 | The muscular tissue around injection area is full of flexibility and luster, no significant change | The muscular tissue around injection area is full of flexibility and luster, no significant change |
| 8 | The muscular tissue around injection area is full of flexibility and luster, no significant change | The muscular tissue around injection area is full of flexibility and luster, no significant change |

TABLE 16 the exciting reaction of rabbits' muscle (sickness investigation) for the biphenyl acetic ammonia butantriol salt injection (high dosage)

| Animal. No. | Left leg quadriceps muscle (reagent side) | Right leg quadriceps muscle (control side) |
|---|---|---|
| 1 | The structure of muscle tissue is normal, and the muscle fiber is very tidily arranged | The structure of muscle tissue is normal, and the muscle fiber is very tidily arranged |
| 3 | The structure of muscle tissue is normal, and the muscle fiber is very tidily arranged | The structure of muscle tissue is normal, and the muscle fiber is very tidily arranged |
| 4 | The structure of muscle tissue is normal, and the muscle fiber is very tidily arranged | The structure of muscle tissue is normal, and the muscle fiber is very tidily arranged |
| 6 | The structure of muscle tissue is normal, and the muscle fiber is very tidily arranged | The structure of muscle tissue is normal, and the muscle fiber is very tidily arranged |

TABLE 17 the exciting reaction of rabbits' muscle (sickness investigation) for the biphenyl acetic ammonia butantriol salt injection (low dosage)

| Animal No. | Left leg quadriceps muscle (reagent side) | Right leg quadriceps muscle (control side) |
|---|---|---|
| 2 | The structure of muscle tissue is normal, and the muscle fiber is very tidily arranged | The structure of muscle tissue is normal, and the muscle fiber is very tidily arranged |
| 5 | The structure of muscle tissue is normal, and the muscle fiber is very tidily arranged | The structure of muscle tissue is normal, and the muscle fiber is very tidily arranged |
| 7 | The structure of muscle tissue is normal, and the muscle fiber is very tidily arranged | The structure of muscle tissue is normal, and the muscle fiber is very tidily arranged |
| 8 | The structure of muscle tissue is normal, and the muscle fiber is very tidily arranged | The structure of muscle tissue is normal, and the muscle fiber is very tidily arranged |

TABLE 18 the test of stomach channel

| Group | Dosage (mg/kg) | Number of ulcer animals/Sum of total animals |
|---|---|---|
| The biphenyl acetic ammonia butantriol salt | 333 | 7/15 |
| Biphenyl acetate | 212 | 13/15 |

What is claimed is:

1. A method of providing anti-inflammatory, analgesic and antipyretic effect on a living object comprising administering a composition of biphenyl acetic ammonia butantriol salt having a chemical structure of:

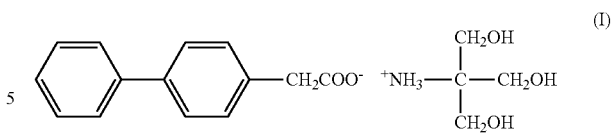

to a living object, wherein said biphenyl acetic ammonia butantriol salt has a molecular weight of 333.14 and a purity greater than 99.5% by weight in said composition.

2. The method, as recited in claim 1, wherein said composition of said biphenyl acetic ammonia butantriol salt is soluble in methanol and methanamide, slightly soluble in water and ethanol and insoluble in propanol and acetonitrile.

3. The method, as recited in claim 2, wherein said composition of said biphenyl acetic ammonia butantriol salt is administered into a living object by injection such that said biphenyl acetic ammonia butantriol salt has anti-inflammatory, analgesic and antipyretic effect on the living object.

4. The method, as recited in claim 1, wherein said biphenyl acetic ammonia butantriol salt is stable in structure and a dosage of said composition of said biphenyl acetic ammonia butantriol salt is adjustable and controllable.

5. The method, as recited in claim 4, wherein said composition of said biphenyl acetic ammonia butantriol salt is in injection form or capsule form.

6. The method, as recited in claim 5, wherein said injection form is selected from the group consisting of injection liquid, injection cool powder and injection aseptic needle.

7. A method of providing anti-inflammatory, analgesic and antipyretic effect on a living object comprising the step of administering a composition consisting essentially of biphenyl acetic ammonia butantriol salt having a chemical structure of:

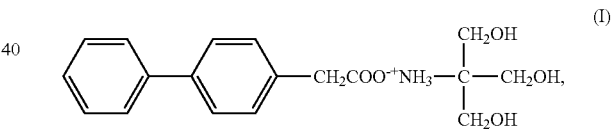

wherein said biphenyl acetic ammonia butantriol salt has a molecular weight of 333.14 and a purity greater than 99.5% by weight in said composition.

8. The method, as recited in claim 7, wherein said composition of said biphenyl acetic ammonia butantriol salt is soluble in methanol and methanamide, and insoluble in propanol and acetonitrile.

9. The method, as recited in claim 8, wherein said composition has anti-inflammatory, analgesic and antipyretic effect.

10. The method, as recited in claim 9, wherein said method further comprises the step of injecting said composition of said biphenyl acetic ammonia butantriol salt into a living object such that said biphenyl acetic ammonia butantriol salt has anti-inflammatory, analgesic and antipyretic effect on the living object.

11. The method, as recited in claim 10, wherein said biphenyl acetic ammonia butantriol salt is stable in structure and a dosage of said composition of said biphenyl acetic ammonia butantriol salt is adjustable and controllable.

12. The method, as recited in claim 11, wherein said composition of said biphenyl acetic ammonia butantriol salt is in injection form or capsule form.

13. The method, as recited in claim 12, wherein said injection form is selected from the group consisting of injection liquid, injection cool powder and injection aseptic needle.

\* \* \* \* \*